United States Patent
Addis et al.

(10) Patent No.: US 6,461,327 B1
(45) Date of Patent: Oct. 8, 2002

(54) ATRIAL ISOLATOR AND METHOD OF USE

(75) Inventors: Bruce Addis, Redwood City; Cynthia Kram, Fremont, both of CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

(21) Appl. No.: 09/131,158

(22) Filed: Aug. 7, 1998

(51) Int. Cl.$^7$ .................. A61M 29/00; A61M 5/178; A61M 5/00; A61M 31/00

(52) U.S. Cl. ................. 604/101.04; 604/102.02; 604/103.03; 604/164.03; 604/164.1; 604/509; 604/8; 606/194

(58) Field of Search .................. 604/96, 98, 101, 604/533, 96.01, 97.01, 99.01, 101.01, 101.03–101.05, 98.01, 102.01–102.03, 532–33.8, 104, 103, 164.01, 164.09–164.1, 264, 523, 500, 506–509; 606/191–192, 194–195, 198; 128/898

(56) References Cited

U.S. PATENT DOCUMENTS

| | | | | |
|---|---|---|---|---|
| 5,411,479 A | * | 5/1995 | Bodden | 604/98 |
| 5,456,673 A | * | 10/1995 | Ziegler et al. | 604/264 |
| 5,462,529 A | * | 10/1995 | Simpson et al. | 604/101 |
| 5,478,309 A | * | 12/1995 | Sweezer et al. | 604/4 |
| 5,728,068 A | * | 3/1998 | Leone et al. | 604/101 |
| 5,820,595 A | * | 10/1998 | Parodi | 604/101 |
| 5,833,650 A | * | 11/1998 | Imran | 604/53 |
| 5,865,801 A | * | 2/1999 | Houser | 604/96 |
| 5,868,708 A | * | 2/1999 | Hart et al. | 604/104 |
| 5,908,407 A | * | 6/1999 | Frazee et al. | 604/101 |
| 5,968,013 A | * | 10/1999 | Smith et al. | 604/102 |
| 5,971,973 A | * | 10/1999 | Peters | 604/509 |
| 6,045,531 A | * | 4/2000 | Davis | 604/101 |
| 6,083,198 A | * | 7/2000 | Afzal | 604/101.01 |
| 6,090,096 A | * | 7/2000 | St. Goar et al. | 604/509 |
| 6,117,105 A | * | 9/2000 | Bresnaham et al. | 604/96.01 |

FOREIGN PATENT DOCUMENTS

WO    WO99/29251    6/1999

* cited by examiner

*Primary Examiner*—Angela D. Sykes
*Assistant Examiner*—P M Bianco
(74) *Attorney, Agent, or Firm*—Lyon & Lyon LLP

(57) ABSTRACT

An atrial isolator comprising two tubular members, two lumens, drainage ports, and expandable occluders. The expandable occluders are adapted to engage an opening of the superior vena cava into the right atrium or the inferior vena cava and right tricuspid valve into the right atrium. The second tubular member is inserted into the lumen of the first tubular member to provide a displacement between the first expandable occluder and the second expandable occluder which is adjustable. A cardioplegia port is located between the two expandable occluders and in communication with a cardioplegic lumen. Methods of using such an atrial isolator are also disclosed, particularly to provide circulatory isolation of the heart and coronary blood vessels, and cardioplegia delivery.

25 Claims, 5 Drawing Sheets

ATRIAL ISOLATOR AND METHOD OF USE

FIELD OF THE INVENTION

The present invention relates generally to devices and methods for performing venous drainage and providing cardiac arrest in cardiac bypass surgery by using an atrial isolator which drains the inferior vena cava and superior vena cava for cardiopulmonary bypass and delivers cardioplegia.

BACKGROUND OF THE INVENTION

Various cardiothoracic surgeries, including coronary artery bypass grafting (CABG), heart valve repair or replacement, septal defect repair, pulmonary thrombectomy, atherectomy, aneurysm repair and correction of congenital defects, generally require cardiopulmonary bypass and cardiac arrest. In order to arrest the heart, the heart and coronary arteries must be isolated from the peripheral vascular system, so that cardioplegia solution can be infused to paralyze the heart without paralyzing the peripheral organs. Cardiopulmonary bypass can be initiated to maintain peripheral circulation of oxygenated blood, and the flow of blood and other fluids can be controlled to provide an optimum surgical environment.

In conventional CABG surgery, circulatory isolation of the heart and coronary blood vessels generally involves opening the right atrial appendage and inserting a two-staged venous cannula, as discussed by Cmolik et al., "Coronary Artery Operations and Reoperations," Cardiothoracic Surgery (1992), incorporated herein by reference. An additional cannula, positioned in the coronary sinus or the ascending aorta, is used to deliver cardioplegia solution after the patient is placed on bypass. Problems associated with this approach are that an extra wound site is required for administering cardioplegia, and that a venous drainage cannula, located in the vicinity of the surgical field, may interfere with a surgeon's operation. In minimally invasive CABG surgery, where small incisions are made in a patient's intercostal space, thereby minimizing trauma to the chest wall from the traditional mid-sternotomy approach, circulatory isolation of the heart and great vessels generally involves insertion of multiple large catheters in either the neck, or the groin, or both to remove blood from the superior vena cava and inferior vena cava for cardiopulmonary bypass. An additional catheter is also required to deliver cardioplegia solution under fluoroscopic guidance. Problems with this procedure are that excessive catheterization and use of fluoroscopy may be associated with increased morbidity.

New devices and methods are therefore desired for isolating the heart and coronary blood vessels from the peripheral vascular system and arresting cardiac function, particularly devices which do not require multiple cannulation sites, fluoroscopy, and/or cardioplegia catheter insertion.

SUMMARY OF THE INVENTION

The present invention provides an atrial isolator having the ability to seal off the atrium by blocking the inferior vena cava, superior vena cava, and tricuspid valve, and drain venous blood to a cardiopulmonary bypass machine, said atrial isolator further having the ability to deliver retrograde cardioplegia through the coronary sinus. The atrial isolator comprises two tubular members, both having a proximal end, a distal end, and an expandable occluder mounted on the distal end. The first tubular member has a drainage port in fluid communication with a lumen. The drainage port is proximal to the expandable occluder, which is adapted to engage an opening of the superior vena cava into the right atrium. The second tubular member has two lumens. A drainage port at the distal end is in fluid communication with the first lumen, and a cardioplegia delivery port located proximal to the drainage port is in fluid communication with the second lumen. The expandable occluder is located between the drainage port and the cardioplegia delivery port, and is adapted to engage an opening of the inferior vena cava and tricuspid valve in the right atrium. The second tubular member is slidably inserted into the lumen of the first tubular member to provide for adjustable displacement between the two expandable occluders. The atrial isolator may further comprise a locking mechanism in its proximal region to lock both occluders at a fixed displacement, so that the atrial isolator can be secured within the right atrium. The proximal end of each tubular member is also adapted for attachment to a cardiopulmonary bypass machine. The atrial isolator of the present invention allows for performance of venous drainage to a cardiopulmonary bypass machine and cardiac arrest by using one cannula system, therefore, obviating the need for multiple catheters.

The present invention also provides methods for venous cannulation for cardiopulmonary bypass during various cardiothoracic surgeries, including CABG. The venous drainage is achieved by sealing the right atrium using the atrial isolator which has (1) a first tubular member comprising a lumen, a first expandable occluder mounted on the distal end, and a drainage port located proximal to the expandable occluder communicating with the lumen, and (2) a second tubular member having first and second lumens, a second expandable occluder mounted on the distal end, a drainage port located distal of the second occluder communicating with the first lumen, and a cardioplegia delivery port located proximal of the second expandable occluder, communicating with the second lumen. An incision is made in a patient's chest wall to provide access to the superior vena cava. The distal end of the atrial isolator is then inserted into the superior vena cava and positioned within the right atrium. The first and second expandable occluders are inflated and the displacement between the two expandable occluders is adjusted so that the first expandable occluder engages an opening of the superior vena cava into the right atrium, while the second expandable occluder engages an opening of the inferior vena cava and tricuspid valve into the right atrium. In this way, blood flow to the right atrium is isolated from the peripheral vascular system. The two expandable occluders can be locked at a fixed displacement by a locking mechanism on the atrial isolator. Venous blood can be withdrawn from the superior vena cava through the drainage port of the first tubular member and from inferior vena through the drainage port of the second tubular member. Once entrance to the right atrium is sealed, cardioplegia solution can be infused through the cardioplegia delivery port into the right atrial chamber and retrograde into the coronary sinus to provide cardiac arrest.

It will be understood that there are many advantages to using an atrial isolator as disclosed herein. For example, the atrial isolator generally (1) requires only one cannulation site for its insertion, (2) does not require thoroscopy to assist in its insertion or positioning within the atrium, (3) achieves venous drainage for cardiopulmonary bypass and cardiac arrest by using one device, negating the need for multiple catheters, (4) is located away from the surgical field, therefore less likely to interfere with a surgeon's operation, and (5) would provide a timed efficient method for venous isolation and cardioplegia delivery in a minimally invasive surgery.

DETAILED DESCRIPTION OF THE INVENTION

The devices and methods disclosed herein can be employed to provide venous drainage for cardiopulmonary bypass and cardiac arrest in a variety of thorascopic, endovascular, or open surgical procedures, including coronary artery bypass grafting, heart valve repair and replacement, septal defect repair, pulmonary thrombectomy, removal of atrial myxoma, patent foramen ovale closure, treatment of aneurysm, myocardial drilling, electrophysiological mapping and ablation, atherectomy, correction of congenital defects, and other interventional procedures. In various pediatric cardiac surgeries, such as atrial septal defects, truncous arteriosis, tetralogy of Fallot, anomalous coronary artery, Ebstein's malformation of the tricuspid valve, heart/lung repair, cardiopulmonary bypass is commonly indicated post-operatively due to a low cardiac output space. The atrial isolator can easily be left in place post-operatively to provide easy access to a cardiopulmonary bypass machine.

Figure 1:
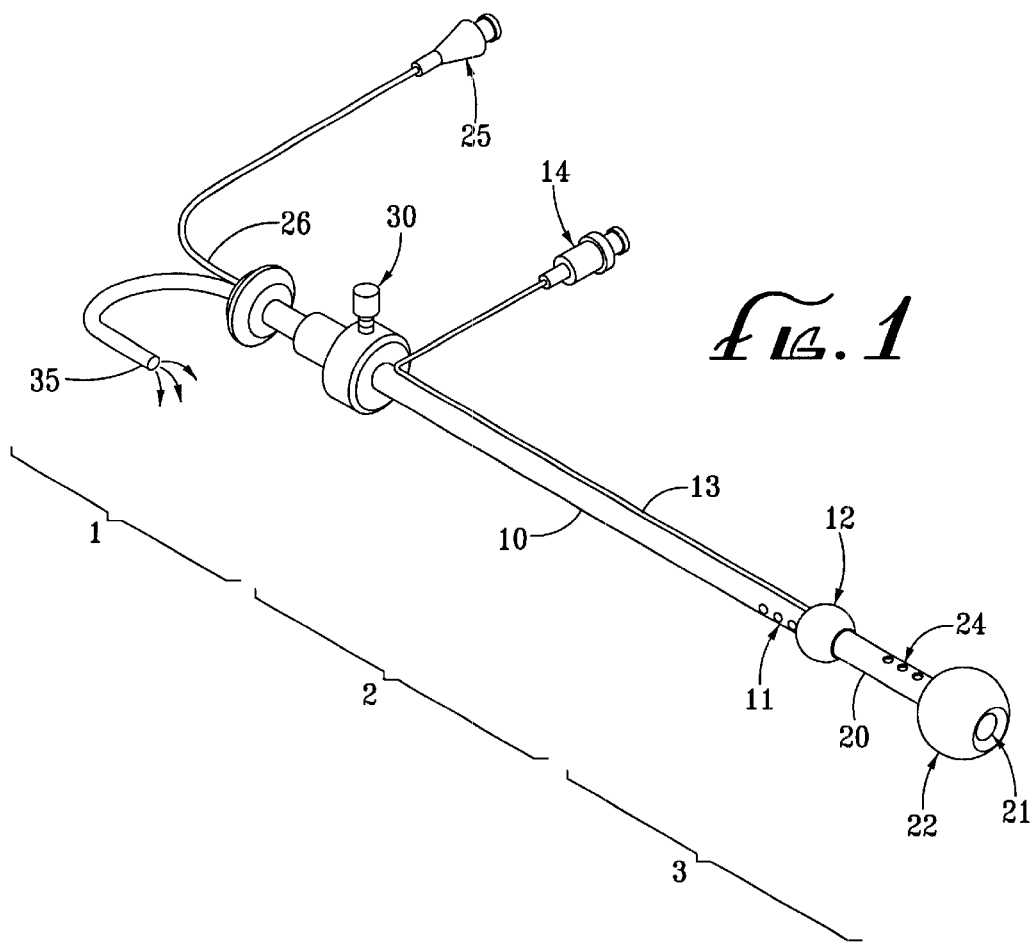
FIG. 1 depicts a preferred embodiment of an atrial isolator according to the present invention.
Figure 5:
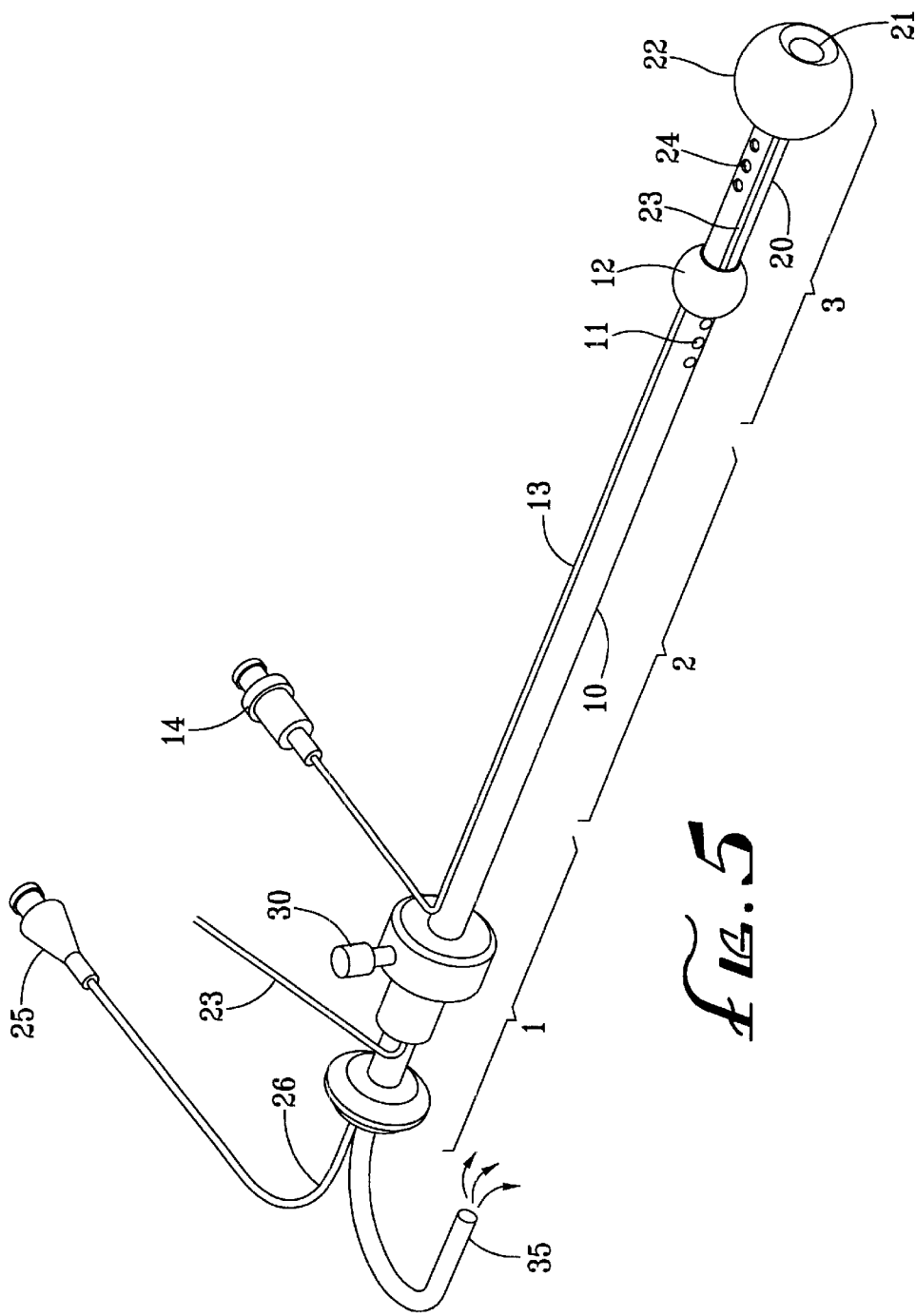
FIG. 5 depicts another embodiment of an atrial isolator according to the present invention.

FIG. 1 depicts a preferred embodiment of an atrial isolator according to the present invention. The atrial isolator has proximal region 1, body 2, and distal region 3, which comprises first tubular member 10 and second tubular member 20. The first tubular member has expandable occluder 12 mounted on its distal end for sealing superior vena cava and venous drainage port 11 located proximal to the expandable occluder for draining superior vena cava. The second tubular member has expandable occluder 22 mounted at its distal region for sealing inferior vena cava and tricuspid valve, cardioplegia port 24 located proximal to the expandable occluder, and venous drainage port 21 at its distal end for draining the inferior vena cava. The proximal region of the atrial isolator comprises sliding locks 30 which lock the two expandable occluders at a fixed displacement, inflation connection 14 which communicates with inflation lumen 13 and inflates expandable occluder 12 (e.g., a balloon occluder), inflation lumen 23 which communicates with and inflates balloon occluder 22 (see FIG. 5), cardioplegia delivery port 25 which communicates with cardioplegia lumen 26 and delivers cardioplegia solution, and venous drainage port 35 which connects to a cardiopulmonary bypass machine.

Figure 2:
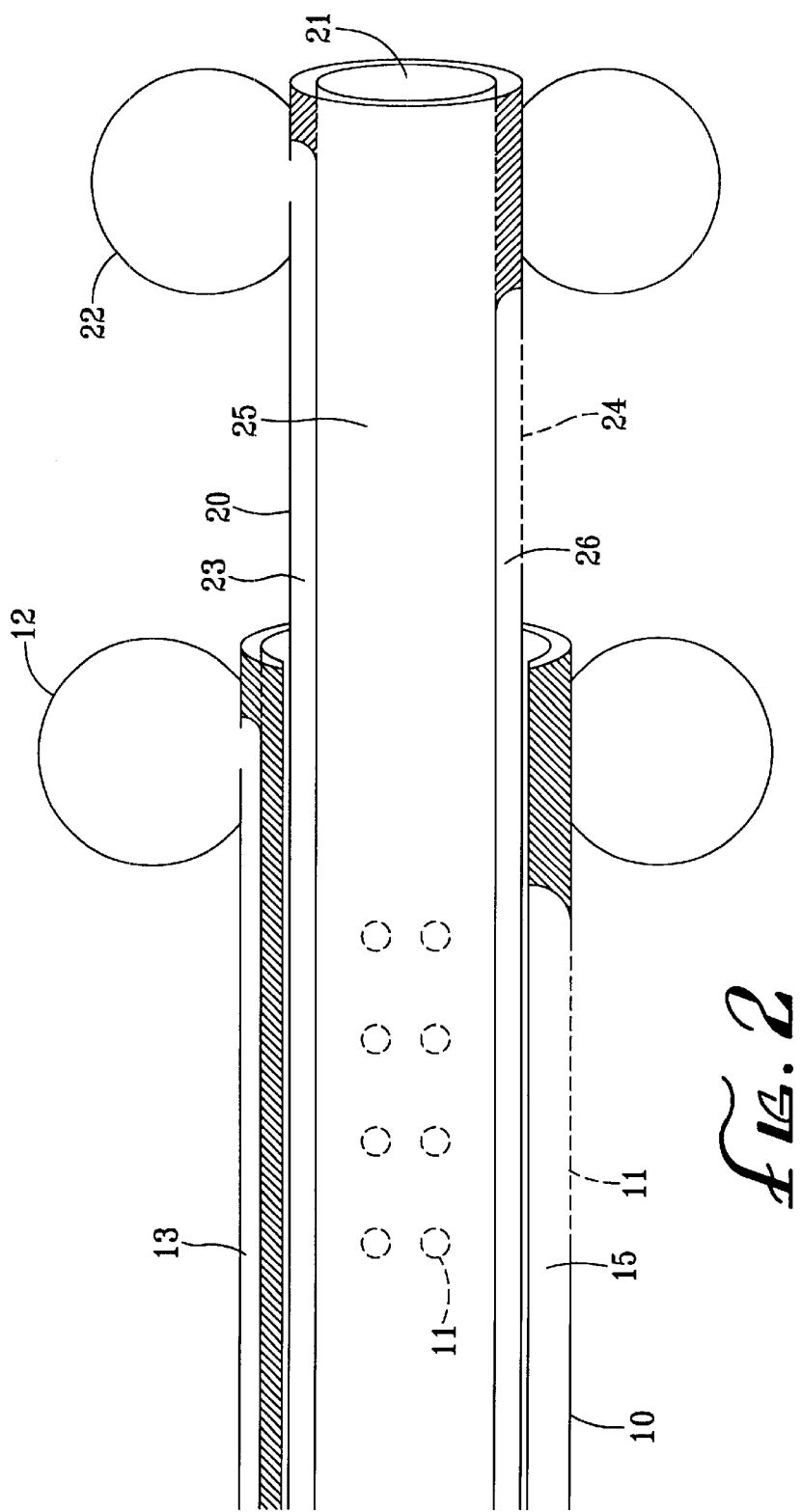
FIG. 2 depicts a longitudinal cross-section of the distal region of the atrial isolator depicted in FIG. 1.

FIG. 2 depicts a side view of the distal region of the atrial isolator depicted in FIG. 1. Second tubular member 20 is slidably inserted into first tubular member 10 to provide for adjustable displacement between expandable occluder 12 and expandable occluder 22. The first tubular member has inflation lumen 13 in communication with expandable occluder 12 and lumen 15 in communication with venous drainage port 11. The second tubular member has inflation lumen 23 in communication with expandable occluder 22, lumen 25 in communication with venous drainage port 21, and lumen 26 in communication with cardioplegia port 24.

Figure 3:
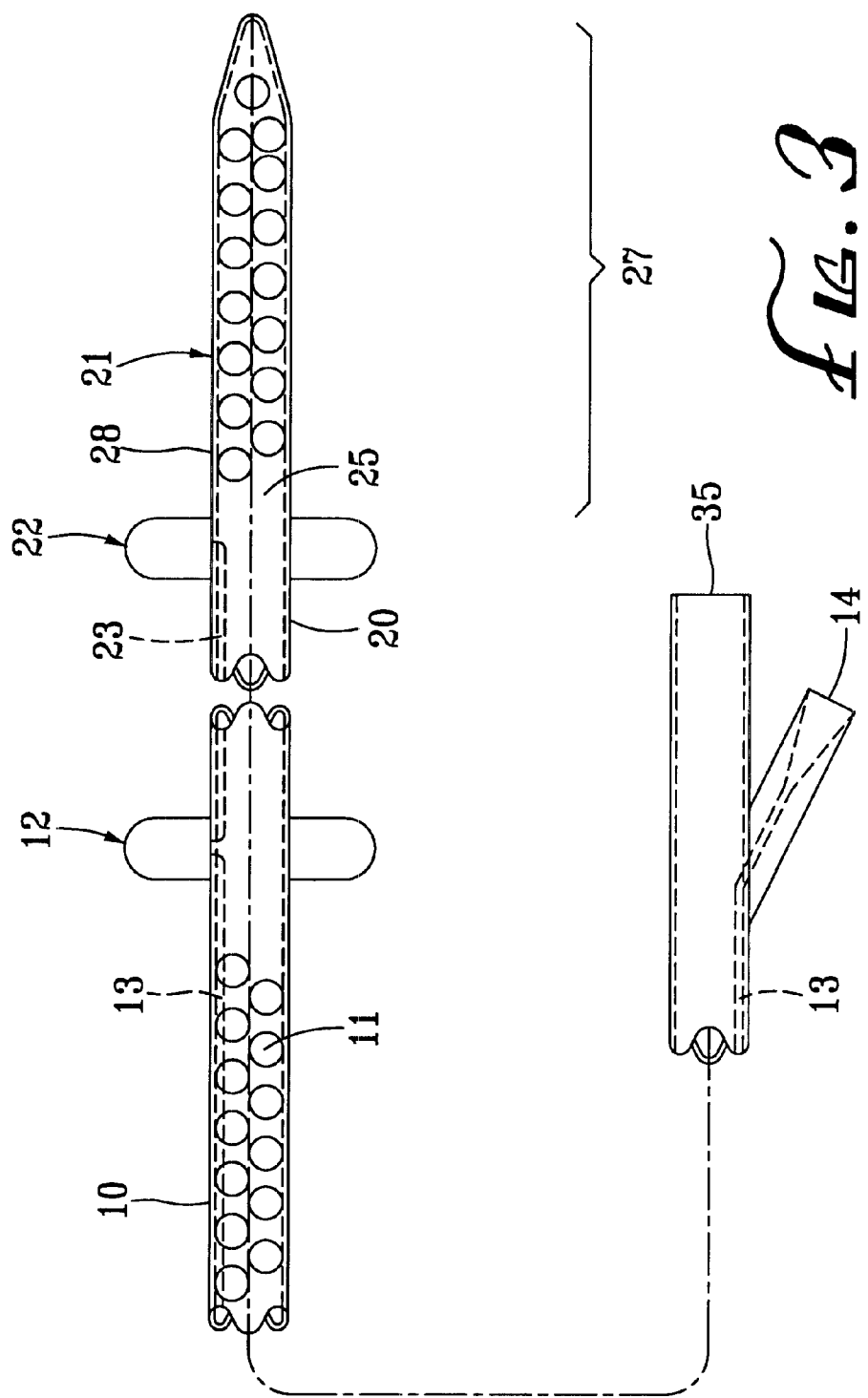
FIG. 3 depicts a longitudinal cross-section of an alternative embodiment of an atrial isolator.

FIG. 3 depicts a side view of an alternative embodiment in which distal region 27 of second tubular member 20 comprises tubular body 28 having a plurality of venous drainage ports 21 distal to expandable occluder 22 for draining the inferior vena cava. In this embodiment, the distal tubular body of the second tubular member is positioned well into a patient's inferior vena cava when the atrial isolator is secured in the right atrium. This is advantageous in that the atrial isolator may provide better venous drainage from the inferior vena cava.

The length of an atrial isolator will generally be between 5 and 30 centimeters, preferably approximately 11 centimeters. The outside diameter of the tubular member will commonly be between 5 and 15 millimeters, preferably approximately 9.5 millimeters. The displacement between the inferior vena and superior vena cava expandable occluders will generally be between 5 and 12 centimeters, preferably approximately 9 centimeters. The outside diameter of the expandable occluder when inflated will commonly be between 1.5 and 4.5 centimeters, preferably approximately 3.0 centimeters. The diameter of the venous drainage port will be between 2 and 5 millimeters, preferably approximately 4.0 millimeters. The foregoing ranges are set forth solely for the purpose of illustrating typical device dimensions. The actual dimensions of a device constructed according to the principles of the present invention may obviously vary outside of the listed ranges without departing from those basic principles.

Figure 4:
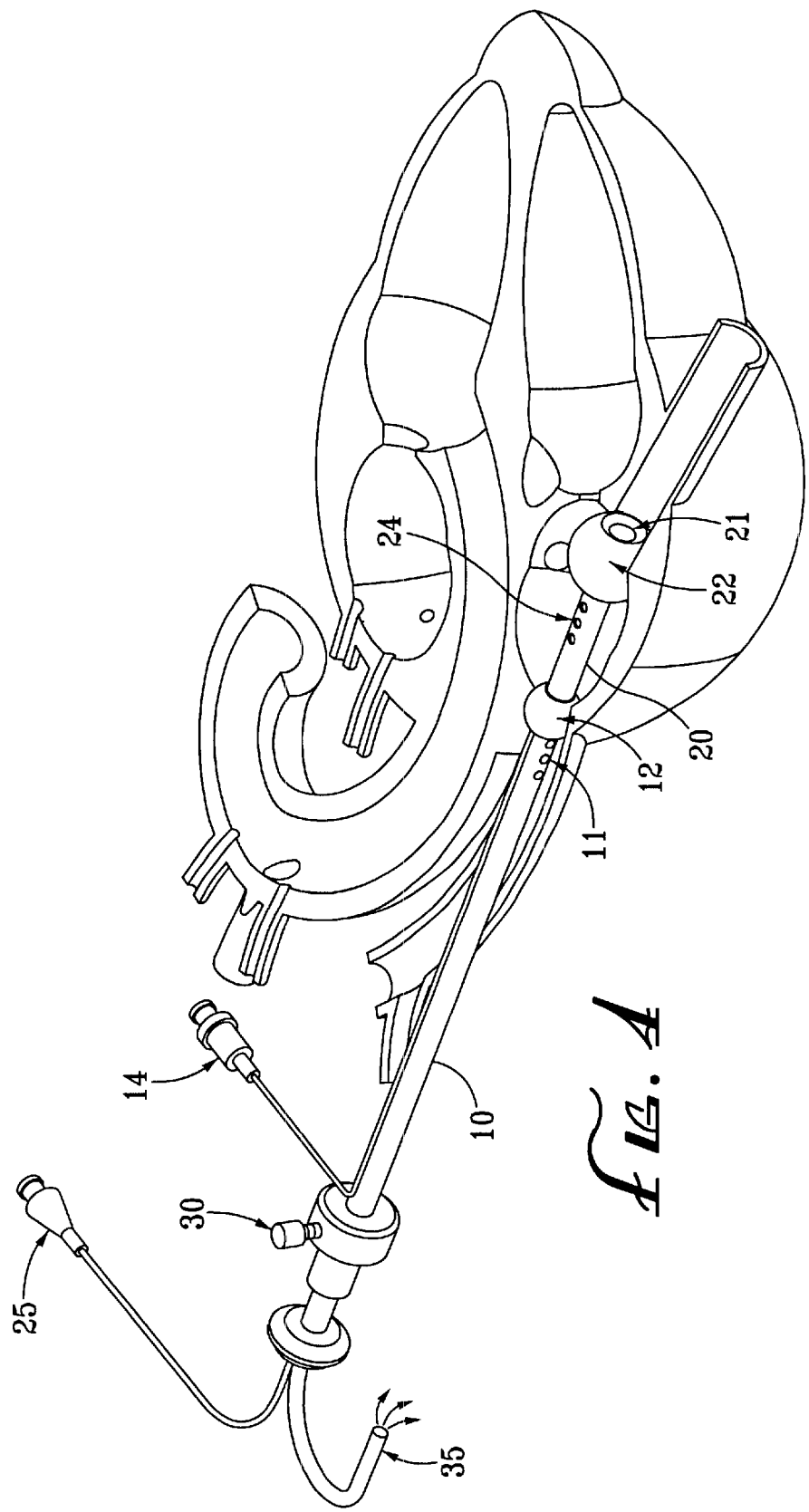
FIG. 4 depicts an atrial isolator positioned within a right atrium.

The methods disclosed herein will be described with reference to FIG. 4, which depicts an atrial isolator positioned within a right atrium. After a patient is under general anesthesia, the superior vena cava is cannulated to allow insertion of the atrial isolator into the right atrium. Expandable occluder 12 is then inflated through inflation connection 14 to engage the opening of the superior vena cava into the right atrium, and expandable occluder 22 is inflated to engage the opening of the inferior vena cava and tricuspid valve into the right atrium. The displacement between the two occluders is adjusted to seal the right atrium. To secure the atrial isolator in the right atrium, the displacement between the two expandable occluders is locked in place by sliding lock 30 after the expandable occluders are positioned as above.

Venous blood from the inferior vena cava and superior vena cava can then be drained, respectively, through venous drainage port 21 on tubular member 20 and venous drainage port 11 on tubular member 10, and be delivered to a cardiopulmonary bypass machine through venous drain 35 in the proximal region of the atrial isolator. The cardiopulmonary bypass machine returns oxygenated blood to the ascending aorta through an arterial cannula, by aortic access, femoral access, or otherwise, and the heart and coronary blood vessels are now isolated from the peripheral vascular system.

Cardioplegia port 24 is situated within the right atrial chamber which is sealed off by the two expandable occluders. In this way, cardiac arrest can be achieved by delivering cardioplegia to the coronary sinus by infusing cardioplegia solution through cardioplegia port 25 to fill the sealed-off atrial chamber. Following delivery of cardioplegia fluid into the coronary sinus, cardiac function will quickly cease. The patient is now prepared for performance of a variety of cardiothoracic surgery, including open-chest and minimally invasive coronary artery bypass grafting.

When it is desired to restore cardiac function, infusion of cardioplegic fluid through the atrial isolator is discontinued. Fluid, blood, and air within the atrium may be aspirated through the cardioplegia port. After reperfusion, the patient is weaned from cardiopulmonary bypass, and the expandable occluders on the atrial isolator are deflated. The atrial isolator is then withdrawn from the superior vena cava, and the wound site is closed.

Although the foregoing invention has, for purposes of clarity and understanding, been described in some detail by way of illustration and example, it will be obvious that certain changes and modifications may be practiced which will still fall within the scope of the appended claims.

What is claimed is:

1. An atrial isolator, comprising:
   a first tubular member having a proximal end, a distal end, and a lumen therebetween, the distal end having one or more drainage ports in fluid communication with the lumen;
   a first expandable occluder mounted on the distal end of the first tubular member and distal to the one or more drainage ports of the first tubular member, the first expandable occluder adapted to engage an opening of the superior vena cava into the right atrium;
   a second tubular member having a proximal end, a distal end, and first and second lumens therebetween, the distal end of the second tubular member having one or more drainage ports in fluid communication with the first lumen of the second tubular member, the distal end of the second tubular member having one or more cardioplegia delivery ports in fluid communication with the second lumen of the second tubular member, the one or more cardioplegia delivery ports located proximal the one or more drainage ports of the second tubular member;
   a second expandable occluder mounted on the distal end of the second tubular member and located between the one or more drainage ports of the second tubular member and the one or more cardioplegia delivery ports, the second expandable occluder adapted to engage an opening of an inferior vena cava and a tricuspid valve into a right atrium; and
   a locking mechanism to lock the first occluder and the second occluder at a fixed displacement,
      wherein the second tubular member is slideably inserted into the lumen of the first tubular member to provide adjustable displacement between the first expandable occluder and the second expandable occluder, and wherein the one or more cardioplegia delivery ports is in fluid communication with a right atrium when the second tubular member is placed to allow the second expandable occluder to engage an opening of an inferior vena cava and a tricuspid valve into a right atrium.

2. The atrial isolator of claim 1, wherein the first and second expandable occluders each comprise a balloon, and the first and second tubular members each comprise a balloon inflation lumen.

3. The atrial isolator of claim 1, wherein said one or more drainage ports of the first tubular member comprises a plurality of drainage ports.

4. The atrial isolator of claim 1, wherein said one or more drainage ports of the second tubular member comprises a plurality of drainage ports.

5. The atrial isolator of claim 1, wherein said one or more cardioplegia delivery ports of the second tubular member comprises a plurality of cardioplegia delivery ports.

6. An atrial isolator, comprising:
   a first tubular member having a proximal end, a distal end, and a lumen therebetween, the distal end having one or more drainage ports in fluid communication with the lumen;
   a first expandable occluder mounted on the distal end of the first tubular member and distal to the one or more drainage ports of the first tubular member, the first expandable occluder adapted to engage an opening of the superior vena cava into the right atrium;
   a second tubular member having a proximal end, a distal end, and first and second lumens therebetween, the distal end of the second tubular member having one or more drainage ports in fluid communication with the first lumen of the second tubular member, the distal end of the second tubular member having a plurality of cardioplegia delivery ports in fluid communication with the second lumen of the second tubular member, the plurality of cardioplegia delivery ports located proximal the one or more drainage ports of the second tubular member; and
   a second expandable occluder mounted on the distal end of the second tubular member and located between the one or more drainage ports of the second tubular member and the one or more cardioplegia delivery ports, the second expandable occluder adapted to engage an opening of an inferior vena cava and a tricuspid valve into a right atrium,
      wherein the second tubular member is slideably inserted into the lumen of the first tubular member to provide adjustable displacement between the first expandable occluder and the second expandable occluder, and wherein the one or more cardioplegia delivery ports is in fluid communication with a right atrium when the second tubular member is placed to allow the second expandable occluder to engage an opening of an inferior vena cava and a tricuspid valve into a right atrium.

7. The atrial isolator of claim 6, wherein the first and second expandable occluders each comprise a balloon, and the first and second tubular members each comprise a balloon inflation lumen.

8. The atrial isolator of claim 6, wherein said one or more drainage ports of the first tubular member comprises a plurality of drainage ports.

9. The atrial isolator of claim 6, wherein said one or more drainage ports of the second tubular member comprises a plurality of drainage ports.

10. The atrial isolator of claim 6, further comprising a locking mechanism to lock the first occluder and the second occluder at a fixed displacement.

11. A method for sealing the atrium of a patient during cardiopulmonary bypass, comprising the steps of:
   providing an atrial isolator comprising a first tubular member having a lumen, a first expandable occluder mounted on the distal end thereof. and one or more drainage ports located proximal the expandable occluder and in fluid communication with the lumen, a second tubular member having first and second lumens, a second expandable occluder mounted on a distal end thereof, one or more drainage ports located distal of the second occluder and in fluid communication with the first lumen, and one or more cardioplegia delivery ports located proximal of the second expandable occluder and in fluid communication with the second lumen;

making an incision in the patient to provide access to the superior vena cava;

inserting a distal end of the atrial isolator into the superior vena cava;

positioning the atrial isolator within the right atrium;

expanding the first and second expandable occluders;

adjusting the displacement between the first and second expandable occluders so that the first expandable occluder engages an opening of a superior vena cava into a right atrium, while the second expandable occluder engages an opening of an inferior vena cava and a tricuspid valve into a right atrium;

locking the first occluder and second occluder at a fixed displacement; and infusing cardioplegia solution into a right atrium through the one or more cardioplegia delivery ports.

12. The method of claim 11, further comprising the steps of withdrawing venous blood from the superior vena cava through the drainage port on the first tubular member and withdrawing venous blood from the inferior vena cava through the drainage port on the second tubular member.

13. The method of claim 11, further comprising the step of infusing cardioplegia retrograde through a right atrium into a coronary sinus.

14. The method of claim 11, wherein the step of providing an atrial isolator comprises providing an atrial isolator wherein the first and second tubular members each have a plurality of drainage ports.

15. The method of claim 11, wherein the step of providing an atrial isolator comprises providing an atrial isolator wherein the second tubular member has a plurality of cardioplegia delivery ports.

16. A method for sealing the atrium of a patient during cardiopulmonary bypass, comprising the steps of:

providing an atrial isolator comprising a first tubular member having a lumen, a first expandable occluder mounted on the distal end thereof, and one or more drainage ports located proximal the expandable occluder and in fluid communication with the lumen, a second tubular member having first and second lumens, a second expandable occluder mounted on a distal end thereof, one or more drainage ports located distal of the second occluder and in fluid communication with the first lumen, and one or more cardioplegia delivery ports located proximal of the second expandable occluder and in fluid communication with the second lumen;

making an incision in the patient to provide access to the superior vena cava;

inserting a distal end of the atrial isolator into the superior vena cava;

positioning the atrial isolator within the right atrium;

expanding the first and second expandable occluders;

adjusting the displacement between the first and second expandable occluders so that the first expandable occluder engages an opening of a superior vena cava into a right atrium, while the second expandable occluder engages an opening of an inferior vena cava and a tricuspid valve into a right atrium; and infusing cardioplegia solution retrograde through a right atrium into a coronary sinus.

17. The method of claim 16, further comprising the steps of withdrawing venous blood from the superior vena cava through the drainage port on the first tubular member and withdrawing venous blood from the inferior vena cava through the drainage port on the second tubular member.

18. The method of claim 16, further comprising the step of locking the first occluder and second occluder at a fixed displacement.

19. The method of claim 16, wherein the step of providing an atrial isolator comprises providing an atrial isolator wherein the first and second tubular members each have a plurality of drainage ports.

20. The method of claim 16, wherein the step of providing an atrial isolator comprises providing an atrial isolator wherein the second tubular member has a plurality of cardioplegia delivery ports.

21. A method for sealing the atrium of a patient during cardiopulmonary bypass, comprising the steps of:

providing an atrial isolator comprising a first tubular member having a lumen, a first expandable occluder mounted on the distal end thereof, and one or more drainage ports located proximal the expandable occluder and in fluid communication with the lumen, a second tubular member having first and second lumens, a second expandable occluder mounted on a distal end thereof, one or more drainage ports located distal of the second occluder and in fluid communication with the first lumen, and a plurality of cardioplegia delivery ports located proximal of the second expandable occluder and in fluid communication with the second lumen;

making an incision in the patient to provide access to the superior vena cava;

inserting a distal end of the atrial isolator into the superior vena cava;

positioning the atrial isolator within the right atrium;

expanding the first and second expandable occluders;

adjusting the displacement between the first and second expandable occluders so that the first expandable occluder engages an opening of a superior vena cava into a right atrium, while the second expandable occluder engages an opening of an inferior vena cava and a tricuspid valve into a right atrium; and infusing cardioplegia solution into a right atrium through the plurality of cardioplegia delivery ports.

22. The method of claim 21, further comprising the steps of withdrawing venous blood from the superior vena cava through the drainage port on the first tubular member and withdrawing venous blood from the inferior vena cava through the drainage port on the second tubular member.

23. The method of claim 21, further comprising the step of infusing cardioplegia retrograde through a right atrium into a coronary Sinus.

24. The method of claim 21, wherein the step of providing an atrial isolator comprises providing an atrial isolator wherein the first and second tubular members each have a plurality of drainage ports.

25. The method of claim 21, further comprising the step of locking the first occluder and second occluder at a fixed displacement.

* * * * *